(12) United States Patent
Siever

(10) Patent No.: US 8,265,761 B2
(45) Date of Patent: Sep. 11, 2012

(54) CRANIAL-ELECTRO STIMULATOR

(76) Inventor: David R Siever, Edmonton (CA)

( * ) Notice: Subject to any disclaimer, the term of this patent is extended or adjusted under 35 U.S.C. 154(b) by 395 days.

(21) Appl. No.: 12/541,959

(22) Filed: Aug. 16, 2009

(65) Prior Publication Data

US 2010/0042181 A1      Feb. 18, 2010

Related U.S. Application Data

(60) Provisional application No. 61/089,728, filed on Aug. 18, 2008.

(51) Int. Cl.
*A61N 1/05* (2006.01)
(52) U.S. Cl. ............................................. 607/46; 607/73
(58) Field of Classification Search .................... 607/46, 607/73
See application file for complete search history.

(56) References Cited

U.S. PATENT DOCUMENTS

| 4,646,744 | A * | 3/1987 | Capel | 607/58 |
| 7,949,403 | B2 * | 5/2011 | Palermo et al. | 607/46 |

* cited by examiner

*Primary Examiner* — Niketa Patel
*Assistant Examiner* — Joseph Stoklosa

(57) ABSTRACT

A method of reducing muscle pain in a person by removably attaching an electrode to each ear on a person's head and connecting the electrodes to receive a modified pulse signal from a computer or a digital port. The signal from the computer or the digital port are rectangular voltage pulses of "1s" and "0s" at varying frequencies. The rectangular pulse signal from the computer or digital port is modified to have at least the leading square corner of each rectangular voltage pulse rounded before it is sent to the electrodes. A method of randomizing the stimulus at about 100 Hz for improved sleep and an alternate method of randomizing stimuli for the neurological reduction of perceived pain and a similar method for reducing pain output from a muscle and its associated tissues directly.

9 Claims, 4 Drawing Sheets

CRANIAL-ELECTRO STIMULATOR

REFERENCE TO RELATED APPLICATION

This patent application claims the benefit of U.S. Provisional Application No. 61/089,728 filed on Aug. 18, 2008, the disclosure of which is incorporated herein by reference in its entirety.

BACKGROUND OF THE INVENTION

1. Field of the Invention

The present invention relates generally to a method and system of electro-biological stimulation and more particularly to method and system, which supports current therapeutic techniques of electro-stimulation.

2. Background of the Invention

Nontraditional procedures that are used to manage pain include the electrical stimulation of tissue. One method of accomplishing this is by attaching electrodes to a person's skin. This procedure, which is generally referred to as trans-cutaneous electro-stimulation (TENS), typically uses a square wave signal with a current that is in the microampere to milliampere range and a frequency that normally varies from under a hertz to about 100 Hertz, which is applied to a select region of a person's anatomy such as, for example, the ear lobes or across a muscle.

SUMMARY OF THE INVENTION

There is disclosed a method and system for treating pain with cranial-electro stimulation (CES) and trans-cutaneous electro-stimulation (TENS) where the pulses of the square wave signal are modified to provide a square wave stimulus edge that is somewhat rounded which provides a more tolerable procedure by reducing the stinging sensation felt from the stimulus.

In an embodiment of the invention the square wave stimuli pulses applied to left and right parts of a person's body are randomized at 100 Hz to reduce habituation.

In an embodiment of the invention randomized left and right electrical stimuli pulses are independently varied between 0.5-3 Hz to reduce habituation of the CES stimuli used for reducing the neurological perception of pain.

In an embodiment of the invention randomized left and right electrical stimuli pulses are independently varied in the 0.5-3 Hz range for treating pain directly over the affected area.

In an embodiment of the invention the method and system of cranial-electro stimulation (CES) is combined with trans-cutaneous electro-stimulation (TENS) for treating muscle pain.

The foregoing has outlined, rather broadly, the preferred feature of the present invention so that those skilled in the art may better understand the detailed description of the invention that follows. Additional features of the invention will be described hereinafter that form the subject of the claims of the invention. Those skilled in the art should appreciate that they can readily use the disclosed conception and specific embodiment as a basis for designing or modifying other structures for carrying out the same purposes of the present invention and that such other structures do not depart from the spirit and scope of the invention in its broadest form.

BRIEF DESCRIPTION OF THE DRAWINGS

Other aspects, features, and advantages of the present invention will become more fully apparent from the following detailed description, the appended claim, and the accompanying drawings.

DETAILED DESCRIPTION OF THE INVENTION

This invention relates to using Cranial-electro Stimulation (CES) to improve sleep and relieve pain. CES is an electrical stimulation technique that has been used for decades. It is officially recognized for the treatment of anxiety, depression and pain. CES is a form of Trans-cutaneous Electro-Stimulation (TENS) in that an electrical stimulus is delivered through a person's skin such as his/her ear lobes. Because the stimuli are delivered specifically via the person's ear lobes and across his/her cranium, the Food & Drug Administration (FDA) has classified this particular type of stimulation as CES.

It is generally believed that Cranial-electro Stimulation, when operating at 100 Hz, can result in an increase of serotonin production and, therefore, can be beneficial in reducing anxiety and depression and, at the same time, augment sleep. Low frequency CES pulse signals have been found to increase endorphin production and, therefore, may be beneficial in reducing the perception of pain.

Typically, electrical stimulation in the form of a square wave pulse signal is obtained from a computer or a logic port. All logic ports generate digital "1s" and "0s" where the digital 1s have a potential of the power supply voltage, and the digital 0s are at zero voltage. These voltage transitions are amplified into much larger voltages needed to produce the current necessary for biological stimulation. However, the amplified voltages continue to exactly follow the digital signals, unless the digital signals are conditioned.

Digital ports switch at a speed that is typically faster then a microsecond. Whenever there is a sharp transition or corner in the waveform, harmonics are generated. It is believed that the harmonics, which are produced by the square wave 1s and 0s cause a stinging sensation in the skin of a person at the site of the electrode which is felt mainly during negative voltage transitions.

It has been determined that much of the sting and discomfort can be eliminated by rounding the square corner from 10-30% without degrading the effectiveness of the stimulus.

Figure 1:
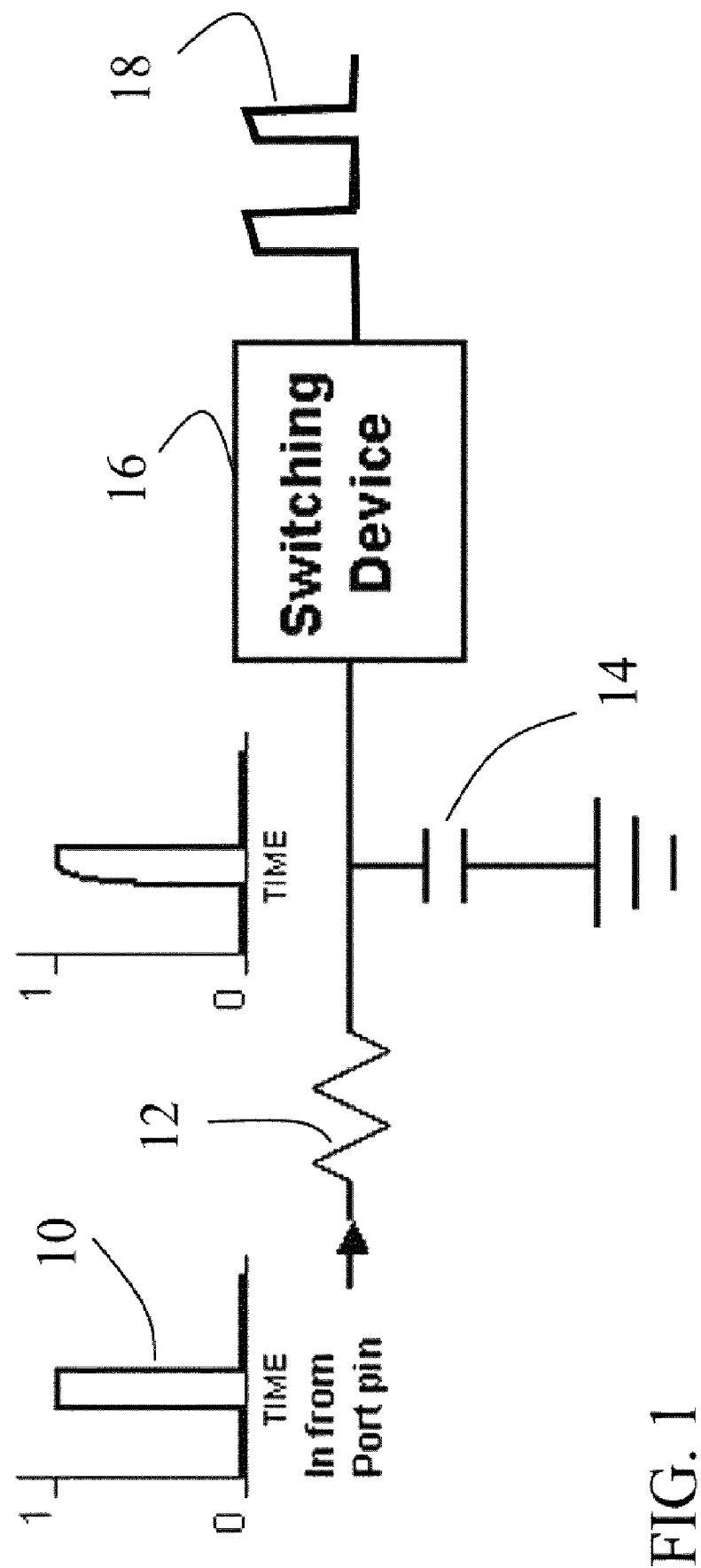
FIG. 1 is a schematic diagram of a circuit that can be used to round the corner of a square wave pulse by implementing a low-pass filter.
Figure 2:
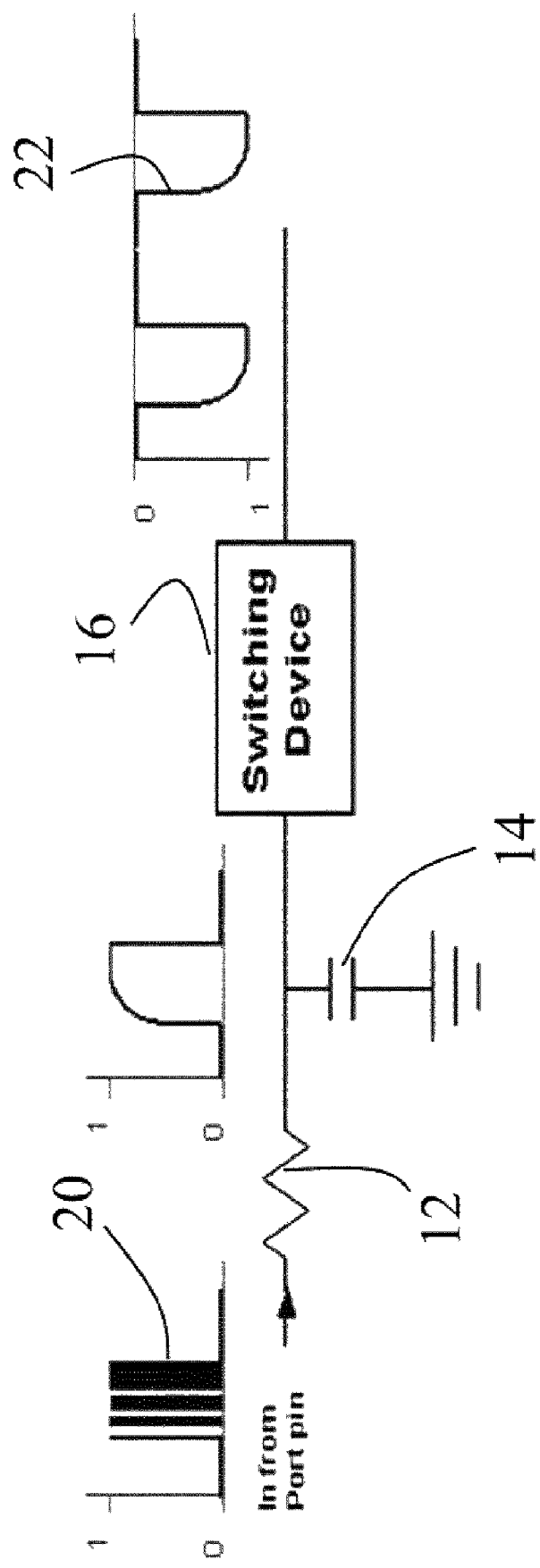
FIG. 2 is a schematic diagram of a circuit that can be used to round the corner of a square wave pulse by implementing a pulse width control signal.

FIG. 1 is a schematic diagram of a circuit that can be used to round the corner of a square wave. The square wave signal 10 from a digital port is fed through a low-pass RC circuit having a resistor 12 and a capacitor 14 to a switching device 16 to produce a square wave signal 18 having a rounded edge. The switching device 16 could be a PNP or NPN transistor or a P-Channel or N-Channel field effect transistor. It can also be an operational amplifier. The square wave stimuli signal can be rounded directly or it can be rounded when connected to a voltage increasing coil or transformer. FIG. 2 shows the same wave rounding circuit of FIG. 1 where the input signal 20 is a pulse-width control signal and the output signal is a square wave signal 22 having a rounded edge.

Randomizing Cranial-Electro Stimulation at 100 HZ

Cranial-electro Stimulation at 100 HZ has been popularized in a number of CES devices manufactured in the past 30 years or so. They typically employ a 0.5 msec., negative going (stimulation) pulse that alternates on each ear every 5 msec., where the cycle is completed every 10 msec., or 100 Hz. The spectral components of such a technique are 2 Khz from the 0.5 msec. pulse itself and 100 Hz in relation to the 10 msec. stimulus repetition rate.

Figure 3:
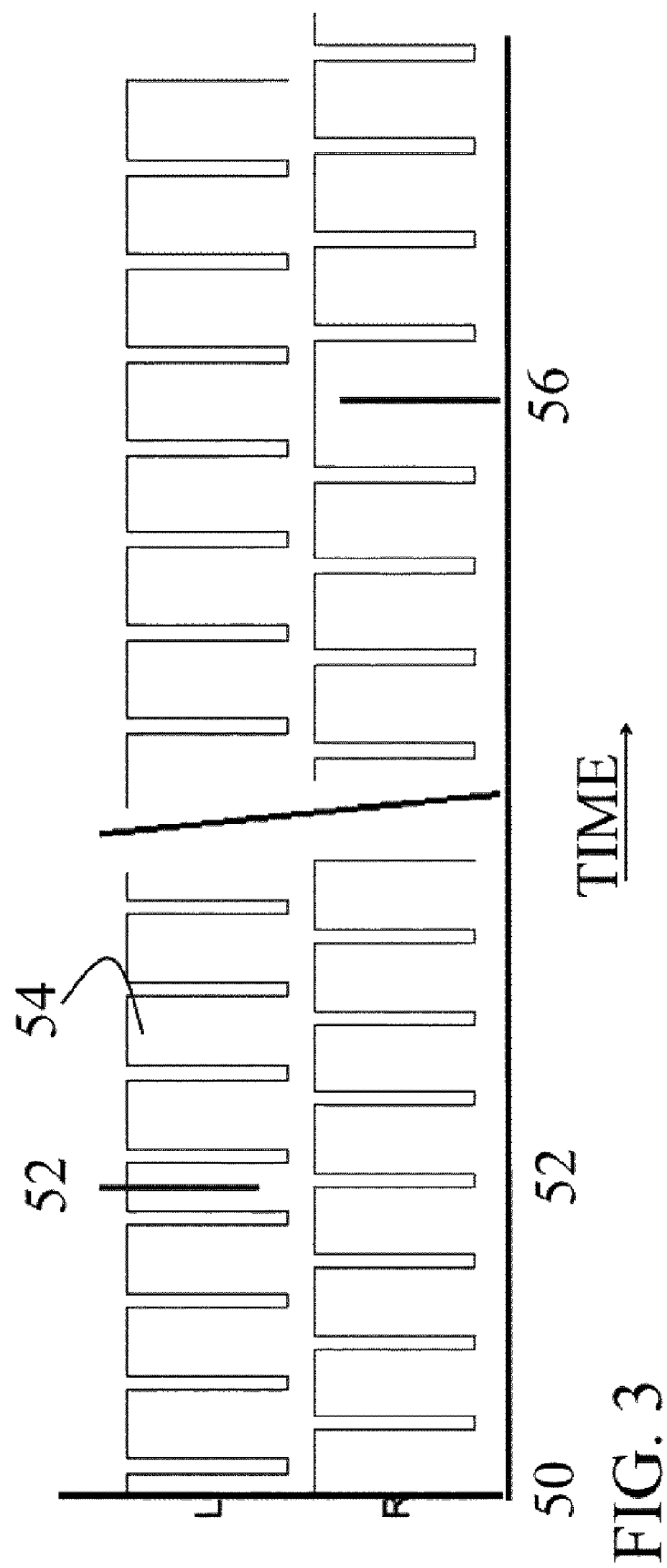
FIG. 3 shows examples of offsetting pulses that are applied to the left and right ear lobes of a person.

The problem with this technique is that a degree of habituation occurs with the steady, repetitive pulse train. By randomly offsetting the alternating left and right pulse intervals, randomly from between 1 to 30 seconds, a wide range of frequency variations are produced which results in an increased effectiveness for improving sleep. Referring to FIG. 3, there are shown examples of offsetting pulses that are applied to the left and right ear lobes of a person. At the start 50 of the pulse stream, the left (L) and right (R) pulses are evenly timed every five milli-seconds. However, at a randomly determined time (52), the left pulse interval is randomly shortened and the next left pulse, 54 starts a bit earlier. Now the left stimuli occurs about 8 msec before the right stimulus. At a random time some seconds later, the right stimulus interval at time 56 is increased causing the left stimulus pulse to occur about 1 msec before the right stimulus pulse occurs. This technique of randomly changing both sides produces harmonics within that side and between both sides.

Randomizing Low Frequency Cranial-Electro Stimulation for Relief of Pain.

Presently low frequency stimulation is achieved by stimulating one ear lobe with one frequency at 0.5 Hz and the other ear lobe at 0.6 Hz, or 0.5 and 0.4 Hz, to generate a 0.1 Hz beat frequency. This beat occurs because, unlike the short pulses used with the 100 Hz method, in this stimulation method, the stimulus duty cycle is 50%. Therefore, both the left and right stimuli constantly interact with each other. When the left side has gone negative, the right side must be positive in order to complete the current loop. Should the right side go negative while the left side is negative, or both sides go positive, the current loop will stop and stimulation will cease until the sides are different from each other. Again, with this method, habituation occurs and the effectiveness is reduced.

To overcome this, there is disclosed a method where both the left and right sides independently generate a stimuli signal at random frequencies between 0.5 and 3 Hz from each other. The stimulation signal should not just "jump" from one frequency to another which can produce a jittery effect, but the frequency should "ramp" up or down in small increments. Over a random period of time, these small increments will add up to produce a significant shift that ranges from 0.5-3 Hz.

Figure 4:
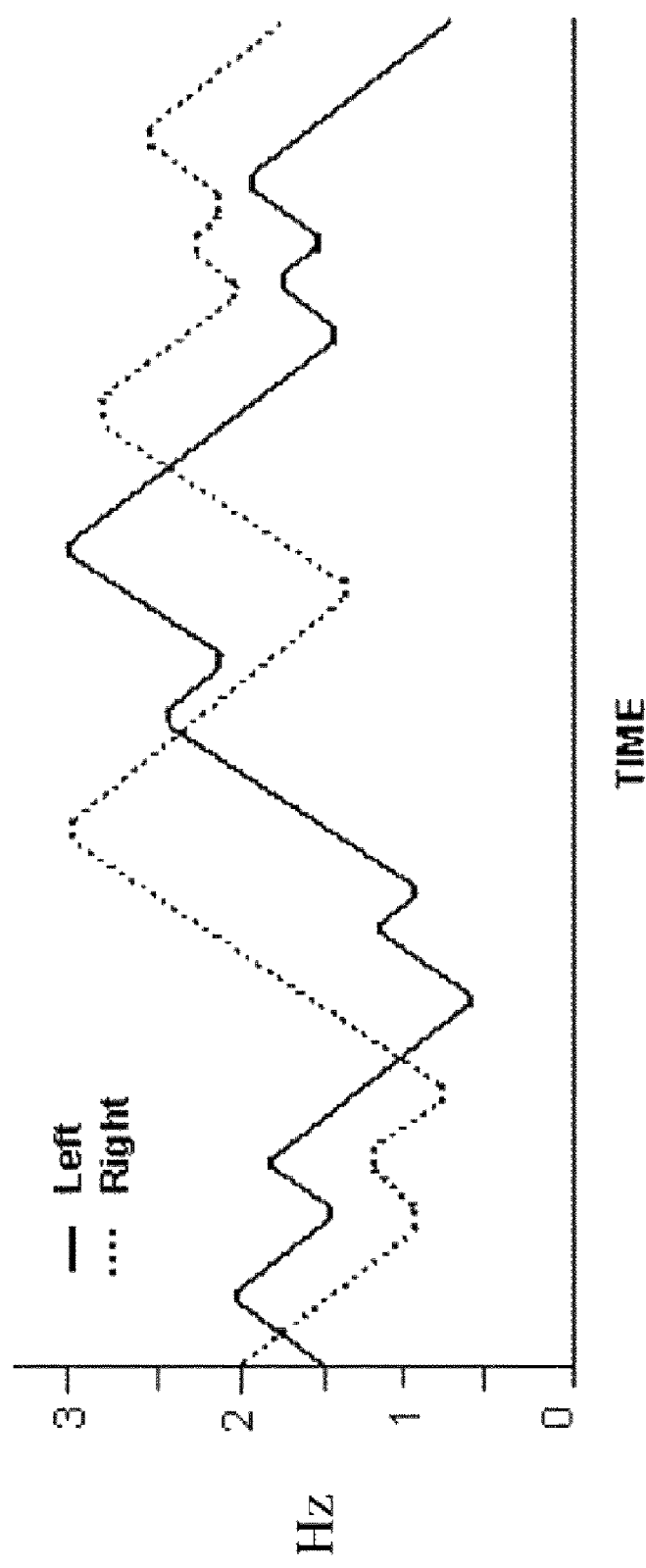
FIG. 4 shows the frequency of the signals to the left and right ears changing at 0.1 Hz/second increments until a target frequency is reached through multiple targets over time.

The small increments can be produced with a random number which can be generated by a microcontroller that indicates the target frequency to approach. The stimuli signal will increase or decrease in 0.1 Hz/second increments until the target is reach. Upon reaching the target, the stimuli signal will stay at the target frequency for a couple of seconds. The timing-loop in software, which is known to those familiar with the art, will then be given another random number and the stimuli signal will again either increase or decrease at a frequency of 0.1 Hz/second until the next target is reached. A random target will be generated in both the left and right sides independent of each other. This is graphically shown in FIG. 4. This method produces a myriad of pulse widths and harmonics, which in turn enhances the effectiveness of a treatment.

Randomizing Low Frequency Trans-Cutaneous Electro-Stimulation (TENS) for Relief of Pain This method employs the same features as explained for Randomizing Low Frequency Cranial-electro Stimulation for Relief of pain, except that this is used on a muscle directly. The pulse width in the case of muscle stimulation (TENS) is short, (<2 msec), in accordance with standard practices.

Traditional stimulators allow for either the stimulation of the nervous system (CES) or stimulation of muscle (TENS). It is here disclosed to have two channels, one channel that provides CES and the associated endorphin production and the other channel that provides simultaneous treatment of a muscle. In this case, the CES duty cycle would be at 50% and the TENS pulse width would be at 2 msec., or less.

Based upon the foregoing, it will be apparent that there has been provided a new and useful method and system to relieve pain.

While there have been shown and described and pointed out the fundamental novel features of the invention as applied to the preferred embodiments, it will be understood that various omissions and substitutions and changes of the form and details of the apparatus illustrated and in the operation may be done by those skilled in the art, without departing from the spirit of the invention.

What is claimed is:

1. A method of reducing pain in a person comprising:
   removably attaching a first electrode to a left ear on a person's head;
   removably attaching a second electrode to a right ear on the person's head;
   supplying from a computer or a digital port to the first and second electrodes alternating rectangular voltage pulses of "1" and "0s" at a frequency of 100 HZ wherein the "1s" have a potential that is a supply voltage of the computer or digital port and the "0s" have a potential of no volts; and
   randomly offsetting the alternating pulses to the first and second electrodes at intervals from between 1 to 30 seconds to produce harmonics between the left ear and the right ear.

2. The method of claim 1 wherein the pulses to the first and second electrodes are randomly alternating offset relative to each other.

3. The method of claim 2 wherein at a randomly determined interval of time, a pulse interval of the pulses to the first electrode is randomly shortened for a predetermined interval of time and, thereafter, at a random interval of time a pulse interval of the pulses to the second electrode is randomly increased to cause the pulses to the first electrode to occur before the pulses to the second electrode occur.

4. The method of claim 3 wherein the pulses to the first and second electrodes are initially evenly timed and at a random interval of time the pulses to the first electrode are randomly lengthened or shortened to occur before or after the pulses to the second electrode, and thereafter, at a random interval of time the pulses to the second electrode are decreased or increased to cause the pulses to the second electrode to occur before or after the pulses to the first electrode.

5. A method of reducing pain in a person comprising:
   removably attaching a first electrode to a left ear on a person's head;
   removably attaching a second electrode to a right ear on the person's head; and
   supplying from a computer or a digital port to the first and second electrodes rectangular voltage pulses of "1s" and "0s" at random ramped frequencies between 0.5 Hz and 3 Hz from each other, wherein the "1s" have a potential that is a supply voltage of the computer or digital port and the "0s" have a potential of no volts.

6. The method of claim 5 wherein a frequency of the pluses to one of the electrodes is randomly increased or decreased to a target frequency.

7. The method of claim 6 wherein the frequencies of the pulses to the one of the electrodes are increased or decreased in 0.1 Hz/second increments until the target frequency is reached.

8. The method of claim 7 wherein the target frequency is changed after a few seconds.

9. The method of claim 6 wherein a target frequency generated for the left ear is independent of a target frequency generated for the right ear.

* * * * *